(12) United States Patent
Roser et al.

(10) Patent No.: US 12,743,777 B2
(45) Date of Patent: Sep. 22, 2026

(54) ADJUSTING A GRAPHICAL DISPLAY

(71) Applicant: Siemens Healthineers AG, Forchheim (DE)

(72) Inventors: Philipp Roser, Erlangen (DE); Annette Birkhold, Stuttgart (DE)

(73) Assignee: Siemens Healthineers AG, Forchheim (DE)

( * ) Notice: Subject to any disclaimer, the term of this patent is extended or adjusted under 35 U.S.C. 154(b) by 247 days.

(21) Appl. No.: 18/603,642

(22) Filed: Mar. 13, 2024

(65) Prior Publication Data

US 2024/0331148 A1 Oct. 3, 2024

(30) Foreign Application Priority Data

Mar. 30, 2023 (DE) ..................... 10 2023 202 955.3

(51) Int. Cl.
*G06K 9/00* (2022.01)
*G06T 7/00* (2017.01)
(Continued)

(52) U.S. Cl.
CPC ............ *G06T 7/0012* (2013.01); *G06T 15/06* (2013.01); *G09G 5/377* (2013.01); *G16H 30/20* (2018.01); *G16H 30/40* (2018.01); *G06T 2207/30024* (2013.01); *G06T 2207/30101* (2013.01); *G06V 2201/07* (2022.01); *G09G 2320/0626* (2013.01); *G09G 2320/066* (2013.01); *G09G 2320/0666* (2013.01)

(58) Field of Classification Search
CPC ................... G06T 7/0012; G06T 15/06; G06T 2207/30101; G06T 2207/30024; G06V 2201/07; G09G 5/377; G09G 2320/0626; G09G 2320/066; G09G 2320/0666; G16H 30/20; G16H 30/40; A61B 6/463; A61B 6/4441; A61B 6/466; G06F 3/013
See application file for complete search history.

(56) References Cited

U.S. PATENT DOCUMENTS 9,196,091 B2 * 11/2015 Papageorgiou ......... G06T 19/00
2021/0201476 A1 * 7/2021 Prasad ...................... G06T 7/50

OTHER PUBLICATIONS

Xia et al. ("A Novel Lung Nodule Accurate Segmentation of PET-CT Images Based on Convolutional Neural Network and Graph Model", IEEE Access, vol. 11, Published on Mar. 28, 2023, pp. 34015-34031) (Year: 2023).*
(Continued)

*Primary Examiner* — Duy M Dang
(74) *Attorney, Agent, or Firm* — Lempia Summerfield Katz LLC

(57) ABSTRACT

A graphical display is adjusted. A dataset having a map and/or a model of a plurality of anatomical and/or medical objects of an object under examination is acquired. A graphical display of the dataset is visualized by a display. Based on a capturing signal, at least one of the plurality of anatomical and/or medical objects being viewed by a viewer of the graphical display is identified. The capturing signal is provided by a capturing unit embodied to capture a partial area of the graphical display currently being viewed by a viewer and to provide the capturing signal in dependence on the captured partial area. The graphical display of the at least one identified object is adjusted by adjusting a display parameter of the graphical display.

19 Claims, 5 Drawing Sheets

(51) Int. Cl.

| | |
|---|---|
| ***G06T 15/06*** | (2011.01) |
| ***G09G 5/377*** | (2006.01) |
| ***G16H 30/20*** | (2018.01) |
| ***G16H 30/40*** | (2018.01) |

(56) References Cited

OTHER PUBLICATIONS

Luo, Yanlin, et al. "Automated brain extraction and immersive exploration of its layers in virtual reality for the rhesus macaque MRI data sets." DOI: 10.1002/cav.l841 (2018): 1-16.

* cited by examiner

CAP-DS
DS
PROV-ES
VISU-GD
ES
ID-OBJ
ADJ-GD
OBS
N
Y
PROV-WF

RU
ES
37
38
21
34
41
42
25
26
U
31
PRVS
24
33
32
39

ADJUSTING A GRAPHICAL DISPLAY

RELATED APPLICATION

This application claims the benefit of DE 10 2023 202 955.3, filed on Mar. 30, 2023, which is hereby incorporated by reference in its entirety.

FIELD

The present description relates to a computer-implemented method for adjusting a graphical display, a system and a computer program product.

BACKGROUND

To capture complex anatomical objects, for example an organ, hollow organ, tissue, tumor, neurovascular pathologies, and/or medical objects, for example a catheter, guidewire, endoscope, and/or implant, in an object under examination, 3D spatially resolved medical image data and/or model data of the object under examination can be captured and graphically displayed to a medical viewer. Current methods reconstruct 3D datasets, for example 3D digital subtraction angiography (DSA), based on a cubic field of view (FOV). Disadvantageously, anatomical and/or medical objects arranged along a viewing direction in front of the anatomical and/or medical objects of interest of the object under examination can at least partially overlay and/or obscure the objects of interest in the graphical display. This can adversely affect procedure planning and/or diagnosis of the object under examination.

SUMMARY AND DESCRIPTION

It is therefore the object to ensure that a plurality of anatomical and/or medical objects of an object under examination can be captured in a graphical display.

According to one approach, the object is achieved by the subject matter of the independent claims. Advantageous embodiments with expedient developments are the subject matter of the subclaims. Irrespective of the grammatical gender of specific terms, they also include individuals with male, female or other gender identities.

In a first aspect, a computer-implemented method is provided for adjusting a graphical display. In an act a), a dataset having a map and/or a model of a plurality of anatomical and/or medical objects of an object under examination is captured. In a further act b), a graphical display of the dataset is visualized by the display unit. In a further act c), at least one of the plurality of anatomical and/or medical objects is identified based on a capturing signal, wherein the at least one object is being viewed by a viewer of the graphical display. Herein, the capturing signal is provided by a capturing unit embodied to identify a partial area of the graphical display which is currently being viewed by the viewer and to provide the capturing signal in dependence on the identified partial area. In a further act d), the graphical display of the at least one identified object is adjusted by adjusting a display parameter of the graphical display.

Advantageously, the above-described acts a) to d) can be executed at least partially, in particular completely, one after the other or simultaneously. In addition, the above-described acts a) to d) can be at least partially, in particular completely, computer-implemented.

The object under examination can, for example, be a human and/or veterinary patient and/or an examination phantom. The viewer can be a staff member, in particular a medical staff member, for example a physician.

Capturing the dataset can include receiving and/or recording the dataset. The reception of the dataset can in particular include capturing and/or reading a computer-readable data memory and/or receiving it from a data memory unit, for example a database. Furthermore, the dataset can be provided by a provision unit of a medical imaging device. Alternatively, or additionally, the dataset can be recorded by the medical imaging device.

The medical imaging device for recording the dataset can include a medical X-ray device, in particular a medical C-arm X-ray device and/or a cone-beam computed tomography system (cone-beam CT, CBCT), a computed tomography system (CT system), a magnetic resonance imaging system (MRI system), a positron emission tomography system (PET system), and/or an ultrasound device.

The dataset can have a map and/or a model, in particular in each case a map and/or in each case a model, of the plurality of anatomical and/or medical objects of the object under examination. The object under examination can have at least one anatomical object, in particular a plurality of anatomical objects, and at least one medical object, in particular a plurality of medical objects. Alternatively, the object under examination can have a plurality of anatomical objects or a plurality of medical objects. The at least one anatomical object can include a vascular portion, a hollow organ, an organ, and/or a tissue of the object under examination. Furthermore, the at least one medical object can include a diagnostic, surgical instrument, and/or an implant arranged in or on the object under examination.

Advantageously, the dataset can have a two-dimensionally (2D) and/or three-dimensionally (3D) spatially resolved map of the plurality of anatomical and/or medical objects of the object under examination. The 2D spatially resolved map can map the plurality of anatomical and/or medical objects of the object under examination as a 2D projection. In particular, the map of the plurality of anatomical and/or medical objects of the object under examination can have a plurality of image points, in particular pixels and/or voxels, with image values, in particular attenuation values and/or intensity values that map the plurality of anatomical and/or medical objects. Alternatively, or additionally, the dataset can have a 2D and/or 3D spatially resolved model, for example a volume model, in particular a volume mesh model, and/or a skeletonized model, in particular a central line model, of the plurality of anatomical and/or medical objects of the object under examination. For example, a statistical and/or standardized model can be adjusted to the object under examination based on parameters of the object under examination. Alternatively, or additionally, the model can have been provided based on pre-captured data, for example pre-procedural image data of the object under examination. For example, the model can be embodied as a digital twin of the object under examination. The dataset can also be time-resolved, in particular the dataset can have a time-resolved map and/or a time-resolved model of the plurality of anatomical and/or medical objects of the object under examination.

The display unit can be a monitor, projector, a display, and/or smart glasses embodied to visualize the graphical display of the dataset. The graphical display of the dataset can be spatially resolved in 2D or 3D. In addition, the graphical display of the dataset can be time-resolved, for example as a video and/or sequence.

The capturing unit can be a sensor, in particular an optical, acoustic, electromagnetic, and/or mechanical sensor, embodied to identify the partial area of the graphical display currently being viewed by the viewer. Alternatively, or additionally, the capturing unit can include an input unit or device, for example a keyboard, a pointing device, and/or an input display (touch screen), embodied to capture viewer input. Furthermore, herein, the capturing unit can be embodied to identify the partial area of the graphical display based on the user input. The input can include information for the spatial identification of the partial area. Alternatively, or additionally, the input can include information on geometric transformations of the graphical display, for example rendering, rotation, scaling, translation, zooming, and/or cropping. The partial area can include a spatial section, in particular a coherent spatial section of the graphical display of the dataset. Advantageously, the capturing unit provides the capturing signal in dependence on the identified partial area, in particular having information on the identified partial area. The identification of the partial area of the graphical display currently being viewed by the viewer can take place manually, for example on the basis of input, or automatically, for example based on a captured direction of view of the viewer.

Advantageously, the capturing signal can be used to identify at least one, in particular a plurality, of the plurality of anatomical and/or medical objects, which is being viewed, in particular currently, by the viewer of the graphical display. Advantageously, at least one of the plurality of anatomical and/or medical objects, in particular at least one map and/or at least one model, can be associated with the partial area of the graphical display of the dataset, for example by a spatial correspondence for providing the graphical display of the dataset. Advantageously, the capturing signal can be used to identify the at least one anatomical and/or medical object of the plurality of anatomical and/or medical objects, which is at least partially, in particular mostly or completely, represented in the partial area of the graphical display.

In act d), the display parameter, in particular a plurality of display parameters, of the graphical display of the at least one identified object, in particular the plurality of identified objects, can be adjusted, in particular selectively. Advantageously, the display parameters of the graphical display of the other anatomical and/or medical objects can remain substantially unchanged. The display parameter can include a brightness, a contrast, a transparency, a coloration, and/or a saturation. Advantageously, the graphical display of the at least one identified object can be emphasized, hidden, and/or flagged, in particular marked, by adjusting the display parameter. Advantageously, the display parameter to be adjusted can be automatically specified, in particular identified, or identified based on further viewer input.

The proposed embodiment can advantageously ensure that the plurality of anatomical and/or medical objects can be captured in the graphical display.

In a further advantageous embodiment of the proposed method, acts b) to d) can be executed repeatedly until the occurrence of an abort condition.

Advantageously, the abort condition can specify a maximum number of repetitions of acts c) to d), for example a number of remaining planned procedure acts. Alternatively, or additionally, the abort condition can specify a maximum duration for the repeated execution of acts b) to d), in particular in total. Alternatively, or additionally, viewing, in particular cumulative viewing, all the plurality of anatomical and/or medical objects by the viewer can lead to the occurrence of the abort condition.

By the repeated, in particular gradual, adjustment of the graphical display based on the objects already viewed, the proposed embodiment can enable improved capturability of the other objects in the graphical display.

In a further advantageous embodiment of the proposed method, the dataset can in each case have a 3D map and/or in each case a 3D model of the plurality of anatomical and/or medical objects. Herein, the graphical display can have a 2D projection of the 3D maps and/or 3D models.

Advantageously, the dataset can have in each case a 3D map, in particular a 3D spatially resolved map, and/or a 3D model, in particular a 3D spatially resolved model, for each of the plurality of anatomical and/or medical objects. Advantageously, the 3D maps and/or 3D models of the plurality of anatomical and/or medical objects can be virtually positioned in a 3D spatial arrangement relative to one another, in particular according to their real positioning in the object under examination. Herein, the graphical display can be provided as a 2D projection map of the 3D maps and/or the 3D models of the plurality of anatomical and/or medical objects, for example onto a display plane.

Advantageously, the graphical display can have display points, in particular pixels, with display values, in particular pixel values, representing the 2D projection of the 3D maps and/or the 3D models. The 2D projection map can map the image values and/or model values of the 3D maps and/or 3D models along the 2D projection, in particular along the respective projection direction, onto the display plane, in particular the display values.

In a further advantageous embodiment of the proposed method, the 3D maps and/or 3D models of the plurality of anatomical and/or medical objects along the 2D projection can at least partially overlay and/or obscure one another. Herein, in each case foreground anatomical and/or medical objects can be identified along the 2D projection based on the capturing signal if a plurality of anatomical and/or medical objects in the partial area of the graphical display at least partially overlay and/or obscure one another.

The 3D maps and/or 3D models of the plurality of anatomical and/or medical objects can at least partially overlay and/or obscure one another along the 2D projection, in particular along the projection direction of the 2D projection map onto the display plane. In particular, image values and/or model values of a plurality of different 3D maps and/or 3D models can be mapped onto a display value. The display values can, for example, be determined as a function, for example as a sum and/or product, and/or as a maximum value and/or minimum value of the image and/or model values along the 2D projection.

If a plurality of the 3D maps and/or 3D models are associated with the partial area of the graphical display of the dataset, for example by the spatial correspondence for providing the graphical display of the dataset, in each case the foreground anatomical and/or medical object along the 2D projection can be identified based on the capturing signal. Herein, advantageously the anatomical and/or medical object that is arranged facing the viewer along the 2D projection with respect to the other anatomical and/or medical objects can be identified as the foreground object.

In a further advantageous embodiment of the proposed method, the at least one anatomical and/or medical object can be identified in the 3D map and/or the 3D model by ray-tracing and/or Z-buffering.

Based on the capturing signal, the partial area of the graphical display can advantageously be identified as a 2D spatially limited area within the display plane. The partial area can include a plurality of display points of the graphical display representing the 2D projection. Starting from the partial area, in particular the display points within the partial area, ray-tracing and/or Z-buffering enables the at least one anatomical and/or medical object being viewed by the viewer to be identified. In particular, in the case of a plurality of anatomical and/or medical objects within the partial area, which at least partially overlay and/or obscure one another, the foreground anatomical and/or medical object can be identified by ray-tracing and/or Z-buffering starting from the partial area against the projection direction of the 2D projection.

The proposed embodiment can enable improved, in particular robust, identification of the at least one anatomical and/or medical object being viewed.

In a further advantageous embodiment of the proposed method, capturing the dataset can include recording projection maps of the object under examination with at least partially non-collinear projection directions. Herein, the 3D maps can be reconstructed from the plurality of projection maps.

The imaging device for recording the dataset, in particular the projection maps, can advantageously have a source and a detector, which can be positioned in a defined arrangement with respect to the object under examination, in particular the region of interest. In one embodiment of the medical imaging device as a medical X-ray device, in particular as a medical C-arm X-ray device and/or computed tomography system (CT), the source can be an X-ray source and the detector can be an X-ray detector.

The at least partially non-collinear projection directions can in each case describe a course of a beam, in particular a central and/or middle beam, between the source and the detector, in particular a detector center point, of the medical imaging device at the time when the respective projection maps are recorded. In particular, the projection directions can in each case describe an angulation of the medical imaging device with respect to the object under examination and/or an isocenter, in particular center of rotation, of the defined arrangement of source and detector. Herein, the isocenter can describe a spatial point around which the defined arrangement of source and detector can be moved, in particular rotated, in particular during the recording of the projection maps. Advantageously, the at least partially collinear projection directions can in each case run through the isocenter, in particular common isocenter.

Advantageously, the plurality of projection maps can in each case map the object under examination in 2D spatial resolution. Advantageously, the 3D maps can be reconstructed from the plurality of projection maps in such a way that the 3D maps map the anatomical and/or medical objects in the object under examination in 3D spatial resolution. The reconstruction can, for example, include filtered back projection. In particular, the 3D maps can be reconstructed from the projection maps according to 3D DSA. For this purpose, the projection maps can map the object under examination in a mask phase, in particular uncontrasted, and a fill phase, in particular contrasted. Subtracting the projection maps, in particular the reconstructed 3D maps, of the mask phase from the projection maps, in particular the 3D maps, of the fill phase, enables 3D maps of the contrasted anatomical objects to be provided. In addition, the reconstruction can include spatial, temporal and/or intensity-based windowing of the projection maps and/or the 3D maps, in particular in an automated or user-specific manner.

In a further advantageous embodiment of the proposed method, the capturing unit can have a direction-of-view-capturing unit embodied to capture a current direction of view of the viewer with respect to the graphical display. Furthermore, the partial area of the graphical display currently being viewed by the viewer can be identified based on the direction of view.

The direction-of-view-capturing unit can have a sensor, for example an electromagnetic and/or optical sensor embodied to capture the current direction of view of the viewer, for example by capturing a spatial positioning, in particular current spatial positioning of pupils of the viewer. Advantageously, the direction-of-view-capturing unit can be embodied to capture the direction of view of the viewer of the graphical display, in particular the display plane. The direction of view can describe a spatial dimension along which the viewer is looking. Advantageously, the direction-of-view-capturing unit can be integrated into the display unit and/or arranged in a defined positional relationship to the display unit. Furthermore, the direction-of-view-capturing unit can be embodied to associate the direction of view with at least one display point, in particular a plurality of display points, of the graphical display, in particular on the display plane. The partial area can include the at least one display point associated with the current direction of view. In addition, the partial area can be identified as including a plurality of display points in a specified environment, for example around an associated display point. Alternatively, or additionally, the partial area can be identified as including a plurality of display points, which are viewed by the viewer for a specified viewing duration and/or within a specified viewing interval.

The proposed embodiment can enable a particularly intuitive identification of the partial area of the graphical display.

In a further advantageous embodiment of the proposed method, the display parameter can include a brightness, a contrast, a transparency, a coloration, and/or a saturation.

The adjustment of the display parameter can include increasing or decreasing the brightness, the contrast, the transparency, and/or the saturation of the graphical display of the at least one identified object. Alternatively, or additionally, a coloration of the graphical display of the at least one identified object can be adjusted. Advantageously, the brightness, the contrast, the transparency, the coloration, and/or the saturation of the graphical display of the at least one identified object can be adjusted relative to a brightness, a contrast, a transparency, a coloration, and/or a saturation of the graphical displays of the other anatomical and/or medical objects.

If the graphical display has a 2D projection of the 3D maps and/or 3D models, advantageously, the brightness, the contrast, the transparency, the coloration, and/or the saturation of the 2D projection of the 3D map and/or the 3D model of the at least one identified object can be adjusted, in particular selectively. Advantageously, the display parameter, in particular the brightness, the contrast, the transparency, the coloration, and/or the saturation, of the graphical display of the at least one identified object can be adjusted in such a way that at least partial overlapping and/or obscuration of the graphical display of the other objects is reduced, in particular minimized. Alternatively, or additionally, the display parameter can be adjusted in such a way that the at least one identified object is flagged, in particular marked, as viewed, for example by a dedicated coloration and/or desaturation and/or transparency.

The proposed embodiment can advantageously enable the other, in particular non-viewed anatomical and/or medical objects, in the adjusted graphical display to be captured in an improved manner.

In a further advantageous embodiment of the proposed method, the at least one anatomical object can include a vascular portion, a hollow organ, an organ, and/or a tissue of the object under examination. Furthermore, the at least one medical object can include a diagnostic, surgical instrument, and/or an implant.

The at least one anatomical object can advantageously include a vascular portion, for example an artery and/or vein, and/or a vascular malformation, for example an arteriovenous malformation and/or a nidus, and/or a hollow organ, for example a lung, and/or an organ, for example a liver and/or a heart, and/or a tissue, for example a muscle tissue and/or a bone structure and/or a tumor tissue, of the object under examination.

The at least one medical object can, for example, include a diagnostic and/or surgical instrument, for example a guidewire, a catheter, an endoscope, and/or an implant, for example a stent.

The proposed embodiment can advantageously ensure that the plurality of anatomical and/or medical objects can be captured in the graphical display.

In a further advantageous embodiment of the proposed method, a viewing duration of the partial area of the graphical display can be captured based on the capturing signal. Herein, the at least one object can be identified when a specified threshold value is reached or exceeded by the captured viewing duration.

Advantageously, the time-resolved capturing signal can be used as the basis for determining how long individual spatial areas of the graphical display are viewed by the viewer. Herein, the capturing signal can initially be used as the basis for identifying all viewed areas of the graphical display as candidate partial areas. When the specified threshold value is reached or exceeded by the viewing duration of a candidate partial area, the candidate partial area can be identified as the partial area. Herein, the viewing duration can denote a time during which the partial area of the graphical display is viewed by the viewer.

The threshold value can be specified based on further viewer input, based on statistical viewing durations, and/or specific to the viewer.

The proposed embodiment can enable improved, in particular reliable, identification of the partial area and the at least one viewed anatomical and/or medical object.

In a further advantageous embodiment of the proposed method, it can be checked whether all maps of the plurality of anatomical and/or medical objects in the graphical display have been viewed by the viewer. If the answer is no, a workflow hint can be issued.

Advantageously, the maps of the plurality of anatomical and/or medical objects can be classified as viewed or not viewed, in particular based on the identification in act c). Advantageously, it can be repeatedly, in particular continuously, checked whether all maps of the plurality of anatomical and/or medical objects in the graphical display have been classified as viewed. If the answer is no, in particular if there is a map of an anatomical and/or medical object that is classified as not viewed, the workflow hint can be issued. The workflow hint can include a graphical display, for example a textual hint, a symbol, a geometric object (for example a contour), a voice output, and/or haptic feedback, for example vibration. Advantageously, the workflow hint can be issued by the display unit, a loudspeaker, and/or a vibration motor. The workflow hint can include information on the presence of a map of an anatomical and/or medical object in the graphical display that is classified as not viewed. In addition, the workflow hint can indicate the at least one map classified as not viewed, in particular a position of the map in the graphical display, for example an arrow and/or a contour.

The proposed embodiment can advantageously ensure a complete view of the anatomical and/or medical objects mapped in the graphical display.

In a second aspect, a system includes a capturing unit (sensor or input), a display unit (display) and a provision unit (processor or computer). The provision unit can be embodied to capture a dataset having a map and/or a model of a plurality of anatomical and/or medical objects of an object under examination. The display unit is embodied to visualize a graphical display of the dataset. The capturing unit is embodied to identify a partial area of the graphical display that is currently being viewed by a viewer and to provide a capturing signal in dependence on the captured partial area. The provision unit is furthermore embodied, based on the capturing signal, to provision at least one of the plurality of anatomical and/or medical objects, wherein the at least one object is being viewed by a viewer of the graphical display. The provision unit and/or the display unit are furthermore embodied to adjust the graphical display of the at least one identified object by adjusting a display parameter of the graphical display.

The advantages of the proposed system substantially correspond to the advantages of the proposed method for adjusting a graphical display. Features, advantages, or alternative embodiments can also be transferred to the other claimed subject matter and vice versa.

In a further advantageous embodiment of the proposed system, the system can furthermore include a medical imaging device embodied to receive the dataset.

The medical imaging device for recording the dataset can include a medical X-ray device, in particular a medical C-arm X-ray device, a cone-beam computed tomography system (cone-beam CT, CBCT), a computed tomography system (CT system), a magnetic resonance tomography system (MRI system), a positron emission tomography system (PET system), and/or an ultrasound device (system).

The advantages of the proposed imaging device substantially correspond to the advantages of the proposed method for adjusting a graphical display. Features, advantages, or alternative embodiments can also be transferred to the other claimed subject matter and vice versa.

In a third aspect, a computer program product has a computer program, which can be loaded directly into a memory of a provision unit, with program sections, for executing all acts of a proposed method for adjusting a graphical display when the program sections are executed by the provision unit. Herein, the computer program product can include software with a source code that still has to be compiled and linked or only has to be interpreted or an executable software code that only needs to be loaded into the provision unit for execution. The computer program product enables the method for adjusting a graphical display by a provision unit to be executed quickly, identically repeatedly and robustly. The computer program product is configured such that it can execute the method acts according to the invention by the provision unit.

The computer program product is, for example, stored on a non-transitory computer-readable storage medium or on a network or server from where it can be loaded into the processor of a provision unit, which can be directly connected to the provision unit or embodied as part of the provision unit. Furthermore, control information of the computer program product can be stored on an electronically readable data carrier. The control information of the electronically readable data carrier can be embodied in such a way that it performs a method according to the invention when the data carrier is used in a provision unit. Examples of electronically readable data carriers are DVDs, magnetic tapes or USB sticks on which electronically readable control information, in particular software, is stored. When this control information is read by the data carrier and stored in a provision unit, all embodiments according to the invention of the above-described method can be performed.

An extensively software-based implementation has the advantage that it is also possible to retrofit provision units used to date in a simple way by a software update in order to work in the manner according to the invention. In addition to the computer program, a computer program product of this kind can optionally include additional parts, such as, for example, documentation and/or additional components and also hardware components, such as, for example, hardware keys (dongles etc.) for using the software.

BRIEF DESCRIPTION OF THE DRAWINGS

Exemplary embodiments are shown in the drawings and described in more detail below. In different figures, the same reference symbols are used for the same features.

The figures show.

DETAILED DESCRIPTION

Figure 1:
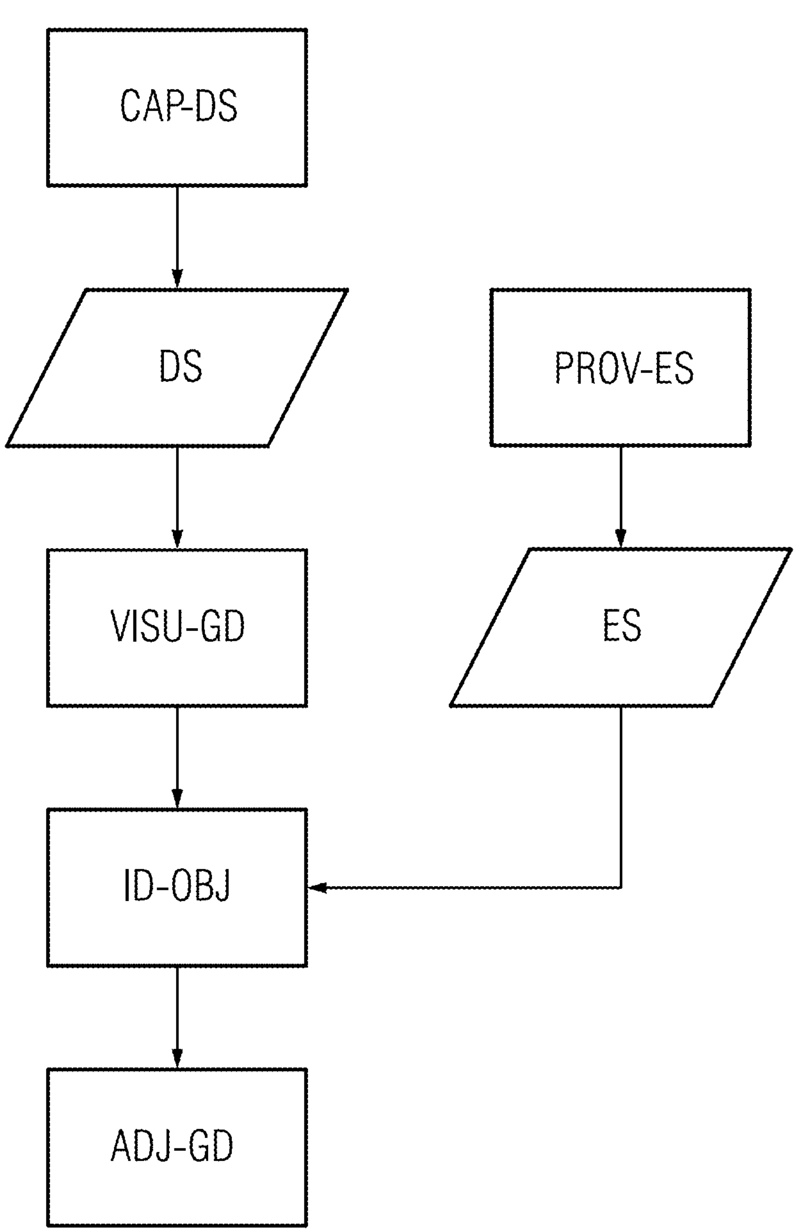
FIGS. 1 to 3—schematic representations of different advantageous embodiments of a computer-implemented method for adjusting a graphical display, and FIGS. 4 and 5—schematic representations of different embodiments of a proposed system.

FIG. 1 is a schematic representation of an advantageous embodiment of a proposed computer-implemented method for adjusting a graphical display. In an act a), a dataset DS having a map and/or a model of a plurality of anatomical and/or medical objects of an object under examination can be captured CAP-DS. The at least one anatomical object can include a vascular portion and/or a hollow organ and/or an organ and/or a tissue of the object under examination. Furthermore, the at least one medical object can include a diagnostic instrument, surgical instrument, and/or an implant. Advantageously, the dataset can in each case have a 3D map and/or in each case a 3D model of the plurality of anatomical and/or medical objects. In particular, capturing the dataset can include recording projection maps of the object under examination with at least partially non-collinear projection directions. Herein, the 3D maps can be reconstructed from the plurality of projection maps.

In a further act b), a graphical display of the dataset DS can be visualized VISU-GD by a display unit. The graphical display can advantageously have a 2D projection of the 3D maps and/or 3D models. Herein, the 3D maps and/or 3D models of the plurality of anatomical and/or medical objects along the 2D projection can at least partially overlay and/or obscure one another. Herein, in each case the foreground anatomical and/or medical object can be identified ID-OBJ along the 2D projection based on the capturing signal ES if a plurality of anatomical and/or medical objects in the partial area of the graphical display at least partially overlay and/or obscure one another. The at least one anatomical and/or medical object can advantageously be identified ID-OBJ by ray-tracing and/or Z-buffering in the 3D map and/or the 3D model.

In a further act c), based on a capturing signal ES, at least one of the plurality of anatomical and/or medical objects being viewed by the viewer can be identified ID-OBJ. Herein, the capturing signal ES can be provided by a capturing unit PROV-ES embodied to identify a partial area of the graphical display and to provide the capturing signal in dependence on the identified partial area. Advantageously, the capturing unit can have a direction-of-view-capturing unit embodied to capture a current direction of view of the viewer with respect to the graphical display. Herein, the partial area of the graphical display currently being viewed by the viewer can be identified based on the direction of view. Advantageously, a viewing duration of the partial area of the graphical display can be captured based on the capturing signal ES. Herein, the at least one object can be identified ID-OBJ when a specified threshold value is reached or exceeded by the captured viewing duration.

In a further act d), the graphical display of the at least one identified object can be adjusted ADJ-GD by adjusting a display parameter of the graphical display. Herein, the display parameter can include a brightness, a contrast, a transparency, a coloration, and/or a saturation.

Figure 2:
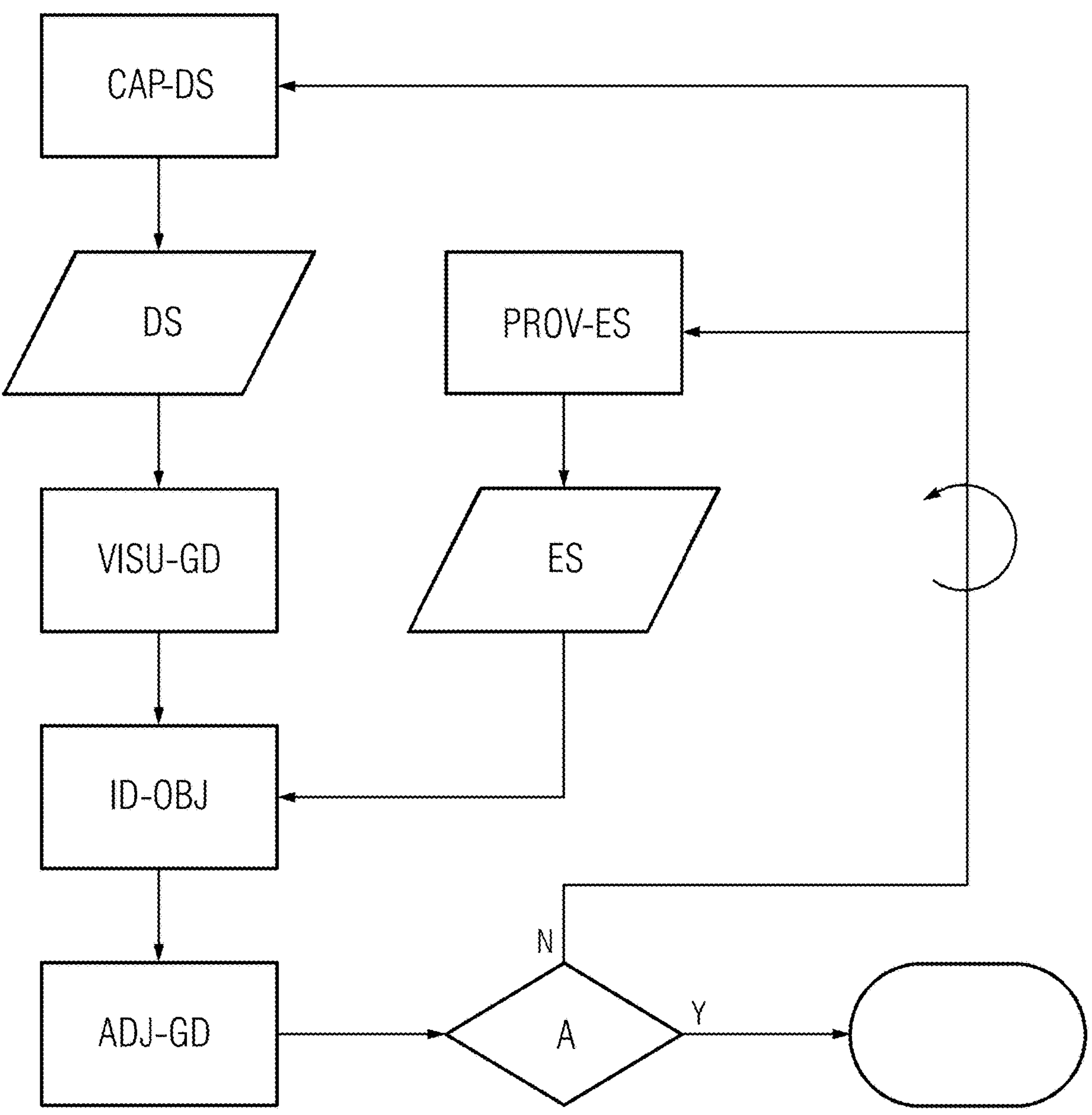

FIG. 2 shows a schematic representation of a further advantageous embodiment of the proposed method for adjusting a graphical display ADJ-GD. Herein, acts b) to d) can be executed repeatedly until the occurrence Y of an abort condition A.

Figure 3:
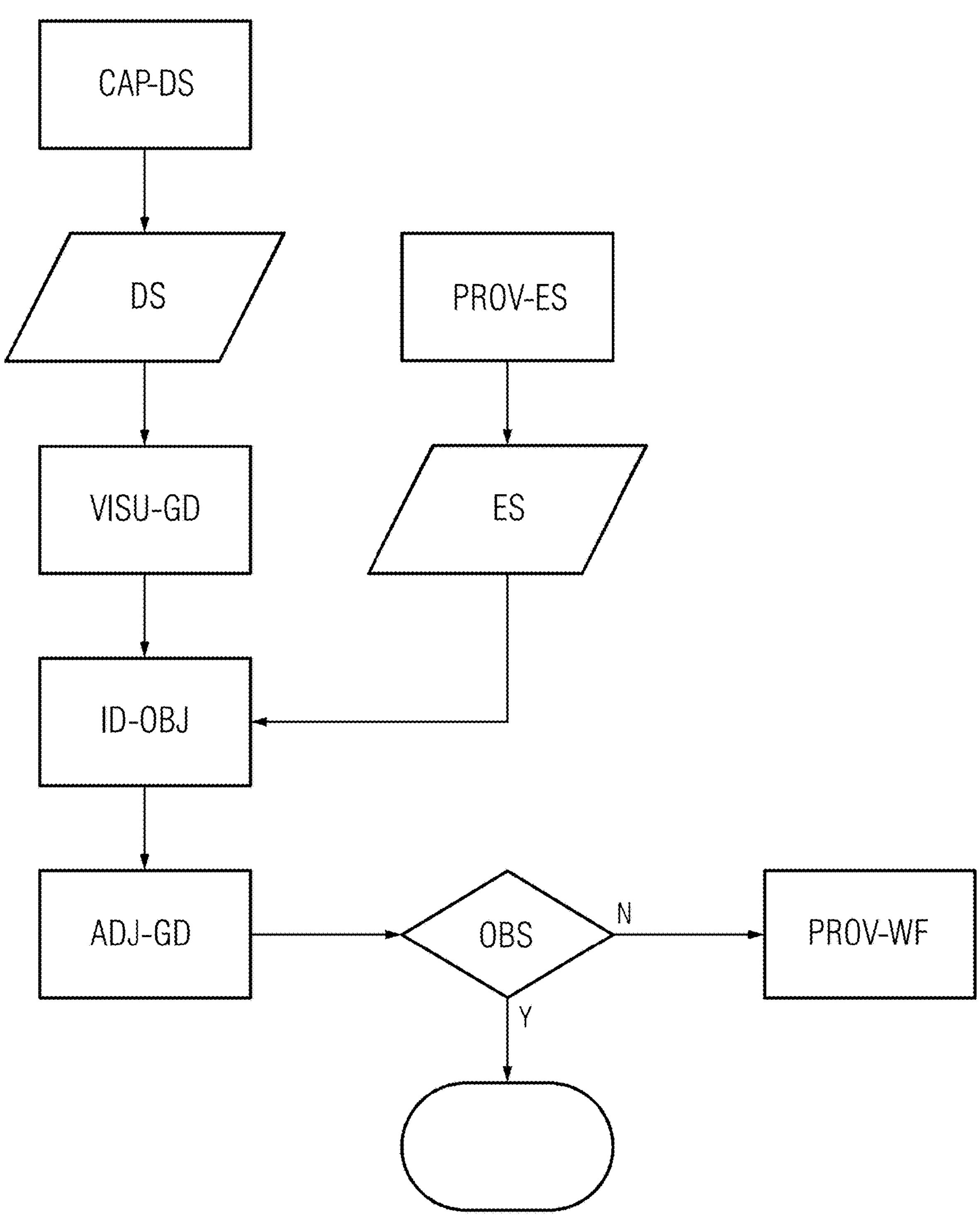

FIG. 3 shows a schematic representation of a further advantageous embodiment of the proposed method for adjusting a graphical display ADJ-GD. Herein, it can be checked OBS whether all maps of the plurality of anatomical and/or medical objects in the graphical display have been viewed by the viewer. If the answer is no N, a workflow hint can be issued PROV-WF.

Figure 4:
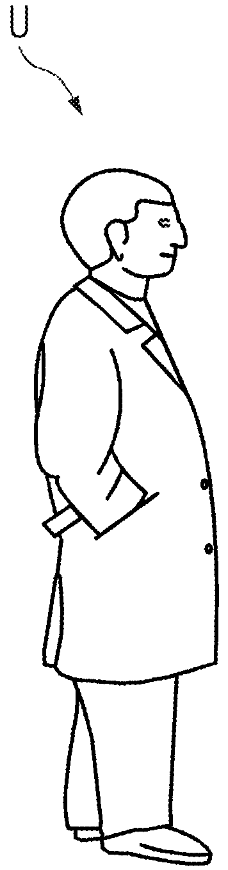
Figure 4:
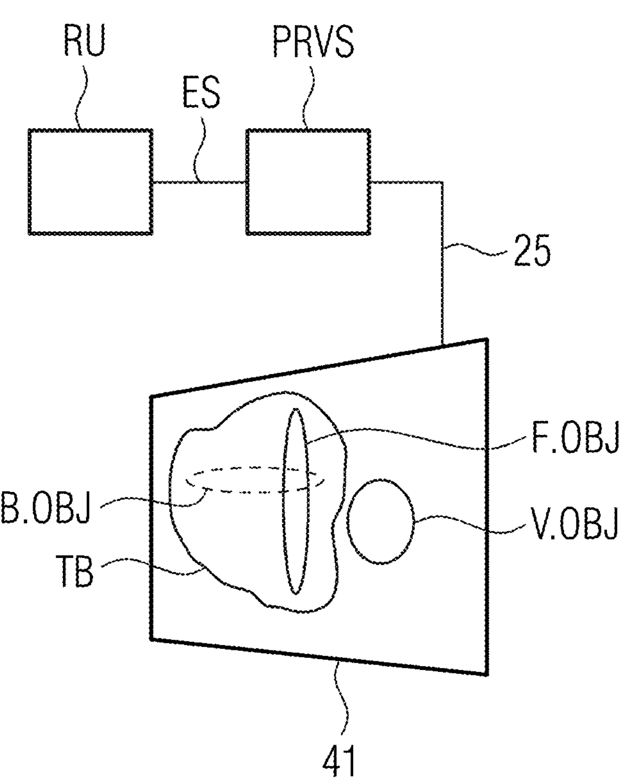

FIG. 4 is a schematic representation of an advantageous embodiment of a proposed system. The system can include a capturing unit RU, a display unit 41, and a provision unit PRVS. The provision unit PRVS can be embodied to capture (acquire) the dataset DS. Furthermore, the display unit 41 can be embodied to visualize the graphical display VISU-GD of the dataset DS. For this purpose, the provision unit PRVS can send a signal 25 to the display unit 41. The display unit 41 can, for example, include a monitor, a display, and/or a projector. Furthermore, the display unit 41 can be embodied to issue the workflow hint PROV-WF. The capturing unit RU can be embodied to identify the partial area TB of the graphical display currently being viewed by the viewer U and to provide the capturing signal ES in dependence on the captured partial area TB. The provision unit PRVS can be embodied, based on the capturing signal ES, to identify ID-OBJ at least one of the plurality of anatomical and/or medical objects being viewed by the viewer U of the graphical display, for example the object F.OBJ. Furthermore, the provision unit PRVS and/or the display unit 41 can be embodied to adjust the graphical display ADJ-GD of the at least one identified object F.OBJ by adjusting the display parameter of the graphical display. For example, the graphical display of a further object B.OBJ already previously viewed by the viewer U can have been adjusted. The graphical display of a further so far unviewed object V.OBJ, lying outside the partial area TB can remain unchanged.

Figure 5:
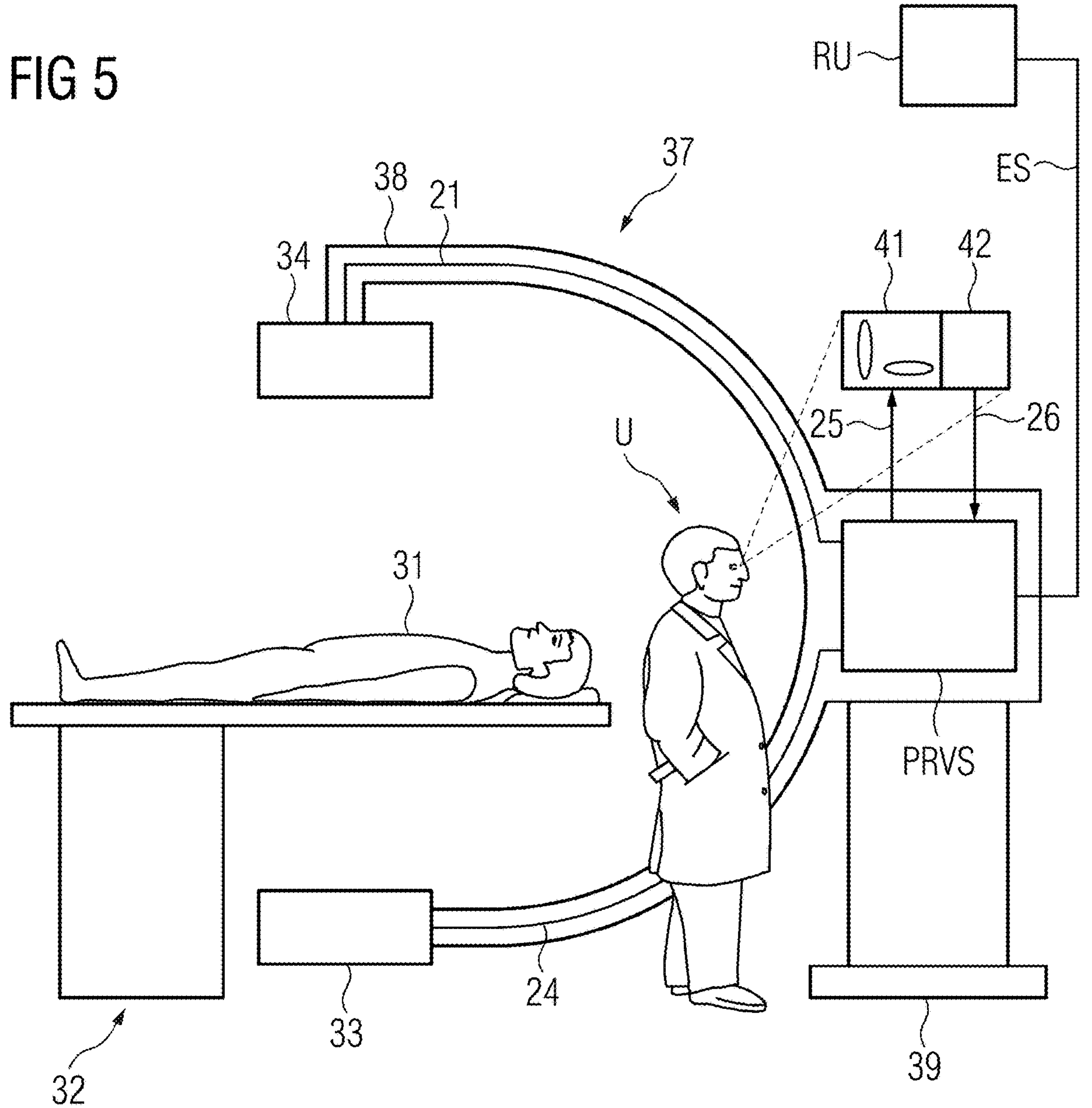

FIG. 5 shows, by way of example for a medical imaging device, a schematic representation of a medical C-arm X-ray device 37, including a provision unit PRVS, a display unit 41 and a capturing unit RU. The medical C-arm X-ray device 37 can advantageously have a detector 34, in particular an X-ray detector, and a source 33, in particular an X-ray source, arranged in a defined arrangement on a C-arm 38. The C-arm 38 of the C-arm X-ray device 37 can be mounted movably about one or more axes. Furthermore, the C-arm X-ray device 37 can include a movement unit 39, for example a wheel system, a robot arm, and/or a rail system, which enables the C-arm X-ray device 37 to move in space. To record projection maps of the object under examination 31 positioned on a patient positioning apparatus 32, the provision unit PRVS can send a signal 24 to the X-ray source 33. The X-ray source 33 can then emit an X-ray beam. When the X-ray beam strikes a surface of the detector 34 after interaction with the object under examination 31, the detector 34 can send a signal 21 to the provision unit PRVS. The provision unit PRVS can map the projection maps based on the signal 21. Herein, the 3D maps can be reconstructed from the plurality of projection maps. In act b), the graphical display of the dataset DS can be visualized VISU-GD by the display unit 41. The graphical display can advantageously have a 2D projection of the 3D maps. For this purpose, the provision unit PRVS can send a signal 25 to the display unit 41.

The imaging device can furthermore have an input unit 42, for example a keyboard. The input unit 42 can preferably be integrated into the display unit 41, for example in the case of a capacitive and/or resistive input display. The input unit 42 can advantageously be embodied to capture viewer input. For this purpose, the input unit 42 can, for example, send a signal 26 to the provision unit PRVS. The provision unit PRVS can be embodied to control the medical C-arm X-ray device, in particular the recording of the projection maps, in dependence on the input, in particular the signal 26. If the viewer does not interact with the graphical display GD for a predefined time duration, in particular identifiable based on the capturing signal ES, the projection maps can be recorded repeatedly by the C-arm X-ray device.

The schematic representations contained in the figures described do not represent any scale or size relationships.

Finally, reference is made once again to the fact that the method described in detail above and the apparatuses shown are merely exemplary embodiments that can be modified in a wide variety of ways by the person skilled in the art without departing from the scope of the invention. Furthermore, the use of the indefinite article "a" or "an" does not preclude the possibility that the features in question may also be present more than once. Likewise, the terms "unit" and "element" do not preclude the possibility that the components in question may consist of a plurality of interacting sub-components which could also be spatially distributed.

In the context of the present application, the expression "based on" can in particular be understood in the sense of the expression "using". In particular a formulation according to which a first feature is generated (alternatively: ascertained, determined, etc.) based on a second feature does not preclude the possibility that the first feature can be generated based (alternatively: ascertained, determined, etc.) on a third feature.

The invention claimed is:

1. A computer-implemented method for adjusting a graphical display (ADJ-GD), the method comprising:

a) capturing a dataset having a map and/or a model of a plurality of anatomical and/or medical objects of an object under examination, b) visualizing a graphical display of the dataset by a display, c) identifying, based on a capturing signal, at least one of the plurality of anatomical and/or medical objects, wherein the at least one of the anatomical and/or medical identified objects is being viewed by a viewer of the graphical display, wherein the capturing signal is provided by a capturing unit embodied to capture a partial area of the graphical display which is currently being viewed by the viewer and to provide the capturing signal in dependence on the captured partial area, and d) adjusting the graphical display of the at least one of the anatomical and/or medical identified objects by adjustment of a display parameter of the graphical display.

2. The computer-implemented method as claimed in claim 1, wherein acts b) to d) are executed repeatedly until occurrence of an abort condition.

3. The computer-implemented method as claimed in claim 1, wherein the dataset has a three-dimensional (3D) map and/or a 3D model of the plurality of anatomical and/or medical objects, and wherein the graphical display has a two-dimensional (2D) projection of the 3D map and/or the 3D model.

4. The computer-implemented method as claimed in claim 3, wherein the 3D maps and/or 3D models of the plurality of anatomical and/or medical objects at least partially overlay and/or obscure one another along the 2D projection, wherein, in each case, a foreground anatomical and/or medical object of the anatomical and/or medical objects along the 2D projection is identified based on the capturing signal when a plurality of the anatomical and/or medical objects in the partial area of the graphical display at least partially overlay and/or obscure one another.

5. The computer-implemented method as claimed in claim 3, wherein the at least one anatomical and/or medical identified object is identified in the 3D map and/or the 3D model by ray-tracing and/or Z-buffering.

6. The computer-implemented method as claimed in claim 3, wherein the capturing of the dataset comprises recording projection maps of the object under examination with at least partially non-collinear projection directions, wherein the 3D map is reconstructed from the plurality of projection maps.

7. The computer-implemented method as claimed in claim 3, wherein the capturing unit captures a current direction of view of the viewer with respect to the graphical display, wherein the partial area of the graphical display currently being viewed by the viewer is identified based on the direction of view.

8. The computer-implemented method as claimed in claim 7, wherein the display parameter comprises a brightness, a contrast, a transparency, a coloration, and/or a saturation.

9. The computer-implemented method as claimed in claim 8, wherein the at least one anatomical object of the object under examination comprises a vascular portion, a hollow organ, a medical object, an organ, and/or tissue of the object under examination and/or wherein the at least one medical object comprises a diagnostic instrument, surgical instrument, and/or an implant.

10. The computer-implemented method as claimed in claim 9, wherein a viewing duration of the partial area of the graphical display is captured based on the capturing signal, wherein the at least one object is identified when a specified threshold value is reached or exceeded by the captured viewing duration.

11. The computer-implemented method as claimed in claim 10, wherein it is checked whether all maps of the plurality of anatomical and/or medical objects in the graphical display have been viewed by the viewer, wherein, when the answer is no, a workflow hint is issued.

12. The computer-implemented method as claimed in claim 1, wherein the capturing unit captures a current direction of view of the viewer with respect to the graphical display, wherein the partial area of the graphical display currently being viewed by the viewer is identified based on the direction of view.

13. The computer-implemented method as claimed in claim 1, wherein the display parameter comprises a brightness, a contrast, a transparency, a coloration, and/or a saturation.

14. The computer-implemented method as claimed in claim 1, wherein the at least one anatomical object of the object under examination comprises a vascular portion, a hollow organ, a medical object, an organ, and/or tissue of the object under examination and/or wherein the at least one medical object comprises a diagnostic instrument, surgical instrument, and/or an implant.

15. The computer-implemented method as claimed in claim 1, wherein a viewing duration of the partial area of the graphical display is captured based on the capturing signal, wherein the at least one object is identified when a specified threshold value is reached or exceeded by the captured viewing duration.

16. The computer-implemented method as claimed in claim 1, further comprising checking whether all maps of the plurality of anatomical and/or medical objects in the graphical display have been viewed by the viewer, , wherein when, based on the checking, not all maps of the plurality of anatomical and/or medical objects in the graphical display have been viewed by the viewer, a workflow hint is issued.

17. A system comprising:

a capturing unit, a display, and a processor configured to capture a dataset having a map and/or a model of a plurality of anatomical and/or medical objects of an object under examination, wherein the display is configured to visualize a graphical display of the dataset, wherein the capturing unit is configured to capture a partial area of the graphical display currently being viewed by a viewer and to provide a capturing signal in dependence on the captured partial area, wherein the processor is configured, based on the capturing signal, to identifying at least one of the plurality of objects, wherein the at least one identified object is being viewed by the viewer of the graphical display, wherein the processor and/or the display are configured to adjust the graphical display of the at least one identified object by adjusting a display parameter of the graphical display.

18. The system as claimed in claim 17, furthermore comprising a medical imaging device configured to generate the dataset.

19. A non-transitory computer readable storage medium having stored there on a computer program, which when executed by a processor causes the processor to:

capture a dataset having a map and/or a model of a plurality of anatomical and/or medical objects of an object under examination, visualize a graphical display of the dataset by a display, identify, based on a capturing signal, at least one of the plurality of anatomical and/or medical objects, wherein the at least one of the anatomical and/or medical identified objects is being viewed by a viewer of the graphical display, wherein the capturing signal is provided by a capturing unit embodied to capture a partial area of the graphical display which is currently being viewed by the viewer and to provide the capturing signal in dependence on the captured partial area, and adjusting the graphical display of the at least one of the anatomical and/or medical identified objects by adjustment of a display parameter of the graphical display.

* * * * *